United States Patent [19]
Long et al.

[11] Patent Number: 5,328,915
[45] Date of Patent: Jul. 12, 1994

[54] ARTHROPODICIDAL AMIDRAZONE UREAS

[75] Inventors: Jeffrey K. Long, Wilmington; Patrick D. Lowder, New Castle; Thomas M. Stevenson, Newark, all of Del.

[73] Assignee: E. I. Du Pont de Nemours and Company, Wilmington, Del.

[21] Appl. No.: 946,988

[22] Filed: Sep. 17, 1992

[51] Int. Cl.$^5$ ............... A01N 43/42; A01N 43/54; C07D 279/10; C07D 239/72
[52] U.S. Cl. .................... 514/310; 514/373; 514/379; 514/416; 514/227.2; 514/230.5; 514/259; 514/226.5; 546/143; 544/90; 544/56; 544/293; 544/63; 544/49; 548/212; 548/241; 548/471
[58] Field of Search ............ 546/143; 514/310, 230.5, 514/373, 379, 416, 227.2, 259, 226.5; 544/90, 56, 293, 63, 49; 548/212, 241, 471

[56] References Cited
FOREIGN PATENT DOCUMENTS
9007495 7/1990 PCT Int'l Appl. ............... 514/310

OTHER PUBLICATIONS

J. Chem. Soc., Peak et al., 4067-75, 1952.
CA 102:6364t The synthesis . . . systems, Dunn, p. 619, 1985.
CA 104:109615w Fungicides, Salzburg et al., p. 725, 1986.

*Primary Examiner*—Mary C. Lee
*Assistant Examiner*—Joseph K. McKane
*Attorney, Agent, or Firm*—James A. Costello

[57] ABSTRACT

Arthropodicidal compounds, compositions and arthropodicidal use of compounds having the formula

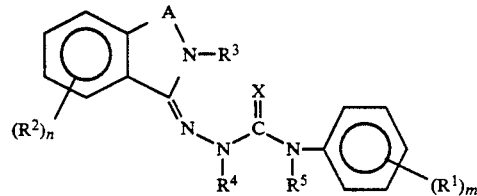

wherein A, X, $R^1$, $R^2$, $R^3$, $R^4$, $R^5$, m and n are as defined in the text.

6 Claims, No Drawings

ARTHROPODICIDAL AMIDRAZONE UREAS

The arthropodicidal amidrazone ureas of this invention are distinguished from the substituted semicarbazones of WO 90/07495 by replacement of a carbon atom of the indane moiety with nitrogen.

SUMMARY OF THE INVENTION

The invention pertains to compounds of Formula I, including all geometric and stereoisomers, agriculturally suitable salts thereof, agricultural compositions containing them and their use to control arthropods in both agronomic and nonagronomic environments. The compounds are:

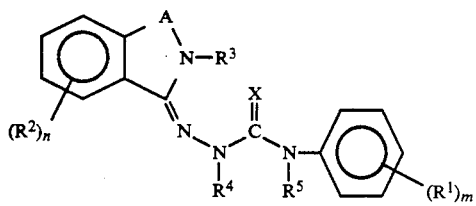

wherein:

A is selected from the group O, $S(O)_q$, $N(R^{10})$, C(O), $CH_2$, $C(CH_2)_v$; $CH_2CH_2$, $CH=CH$, $G-CH_2$, and $G-C(CH_2)_v$, wherein each hydrogen attached to a ring carbon can be optionally replaced with a substituent independently selected from the group halogen, $C_1-C_6$ alkyl, $C_3-C_6$ cycloalkyl, $C_1-C_6$ haloalkyl, $C_3-C_6$ halocycloalkyl, $C_4-C_7$ cycloalkylalkyl, $C_2-C_4$ alkoxycarbonyl and phenyl, wherein phenyl can be optionally substituted with 1 to 3 substituents independently selected from W;

G is selected from the group $N(R^{10})$, $S(O)_q$ and O, wherein when A is $G-CH_2$, or $G-C(CH_2)_v$, the carbon is attached to the phenyl ring or the nitrogen;

X is selected from the group O and S;

$R^1$ and $R^2$ are independently selected from the group H, $C_1-C_6$ alky, $C_1-C_6$ haloalkyl, $C_3-C_6$ cycloalkyl, $C_3-C_6$ halocycloalkyl, $C_4-C_7$ cycloalkylalkyl, $C_4-C_7$ halocycloalkylalkyl, $C_2-C_6$ alkenyl, $C_2-C_6$ haloalkenyl, $C_2-C_6$ alkynyl, $C_2-C_6$ haloalkynyl, $C_2-C_6$ alkoxyalkyl, $C_1-C_6$ alkylthio, $C_2-C_6$ alkylthioalkyl, $C_1-C_6$ nitroalkyl, $C_2-C_6$ cyanoalkyl, $C_3-C_8$ alkoxycarbonylalkyl, halogen, CN, $NO_2$, $N_3$, SCN, $OR^6$, $SR^6$, $S(O)R^6$, $S(O)_2R^6$, $N(R^7)R^8$, $C(O)R^6$, $C(O)OR^6$, $C(O)N(R^7)R^8$, $OC(O)R^6$, $OC(O)OR^6$, $OC(O)N(R^7)R^8$, $N(R^9)C(O)R^7$, $N(R^9)C(O)N(R^7)R^8$, $OS(O)_2R^7$, $N(R^8)S(O)_2R^7$; and phenyl or benzyl each optionally substituted with 1 to 3 substituents independently selected from W; when m is 2, $R^1$ is optionally taken together as $OCH_2O$, $OCH_2CH_2O$ or $CH_2CH_2O$ to form a 5-or 6-membered fused ring, each carbon optionally substituted with 1 or 2 substituents independently selected from the group halogen and methyl; when n is 2, $R^2$ is optionally taken together as $OCH_2O$, $OCH_2CH_2O$ or $CH_2CH_2O$ to form a 5- or 6-membered fused ring, each carbon optionally substituted with 1 or 2 substituents independently selected from the group halogen and methyl;

$R^3$ is selected from the group H, $C_1-C_6$ alkyl, $C_1-C_6$ haloalkyl, $C_2-C_6$ alkylcarbonyl and $C_2-C_6$ alkoxycarbonyl; $C_1-C_6$ alkyl substituted with a group selected from CN, $NO_2$, $C_1-C_4$ alkoxy, $C_1-C_4$ haloalkoxy, $C_1-C_4$ alkylthio and $C_2-C_4$ alkoxycarbonyl; and phenyl and benzyl each optionally substituted with 1 to 3 substituents independently selected from W;

$R^4$ and $R^5$ are independently selected from the group H, $C_1-C_6$ alkyl, $C_1-C_6$ haloalkyl, $C_3-C_6$ cycloalkyl, $C_3-C_6$ halocycloalkyl, $C_4-C_7$ cycloalkylalkyl, $C_4-C_7$ halocycloalkylalkyl, $C_2-C_6$ alkoxyalkyl, $C_2-C_6$ alkenyl, $C_2-C_6$ alkynyl, CHO, $C_2-C_6$ alkylcarbonyl, $C_2-C_6$ alkoxycarbonyl, $C(O)R^{18}$, $C(O)OR^{18}$, $C_1-C_6$ alkylthio, $C_1-C_6$ haloalkylthio, phenylthio, $R^{11}OC(O)N(R^{12})S-$, $R^{13}(R^{14})NS-$, $N=C(R^{15})R^{16}$, $OR^6$, and $N(R^{15})R^{16}$; $C_1-C_6$ alkyl substituted with a group selected from CN, $NO_2$, $C_1-C_4$ haloalkoxy, $C_1-C_4$ alkylthio, $C_1-C_4$ alkylsulfinyl, $C_1-C_4$ alkylsulfonyl, $C_2-C_4$ alkylcarbonyl and $C_2-C_4$ alkoxycarbonyl; and phenyl and benzyl each optionally substituted with 1 to 3 substituents independently selected from W;

$R^6$ and $R^7$ are selected from the group H, $C_1-C_6$ alkyl, $C_1-C_6$ haloalkyl, $C_4-C_7$ cycloalkylalkyl, $C_4-C_7$ halocycloalkylalkyl, $C_2-C_6$ alkenyl, $C_2-C_6$ haloalkenyl, $C_2-C_6$ alkynyl, $C_2-C_6$ haloalkynyl, $C_2-C_6$ alkoxyalkyl, $C_2-C_6$ alkylthioalkyl, $C_1-C_6$ nitroalkyl, $C_2-C_6$ cyanoalkyl, $C_3-C_8$ alkoxycarbonylalkyl, $C_3-C_6$ cycloalkyl and $C_3-C_6$ halocycloalkyl; and phenyl and benzyl each optionally substituted with 1 to 3 substituents independently selected from W;

$R^8$ and $R^9$ are independently selected from the group H, $C_1-C_4$ alkyl, $C_2-C_4$ alkenyl, $C_2-C_4$ alkynyl; or when $R^7$ and $R^8$ are attached to the same atom they can optionally be taken together as $-CH_2CH_2CH_2CH_2-$, $-CH_2CH_2CH_2CH_2CH_2-$ or $-CH_2CH_2OCH_2CH_2-$;

$R^{10}$ is selected from the group H, $C_1-C_6$ alkyl, CHO, $C_2-C_6$ alkylcarbonyl and $C_2-C_6$ alkoxycarbonyl;

$R^{11}$ is $C_1-C_6$ alkyl;

$R^{12}$ is $C_1-C_4$ alkyl;

$R^{13}$ and $R^{14}$ are independently $C_1-C_4$ alkyl; or $R^{13}$ and $R^{14}$ can be taken together as $-CH_2CH_2CH_2CH_2CH_2-$ or $-CH_2CH_2OCH_2CH_2-$;

$R^{15}$ is selected from the group H, $C_1-C_4$ alkyl and $C(O)R^{17}$;

$R^{16}$ is selected from the group H, $C_1-C_4$ alkyl, $C_1-C_4$ haloalkyl; and phenyl optionally substituted with 1 to 3 substituents independently selected from W; or $R^{15}$ and $R^{16}$ can be taken together as $-CH_2CH_2CH_2-$, $-CH_2CH_2CH_2CH_2-$ or $-CH_2CH_2CH_2CH_2CH_2-$;

$R^{17}$ is selected from the group H, $C_1-C_6$ alkyl, $C_1-C_6$ alkoxy, $C_1-C_6$ haloalkyl, $C_2-C_6$ alkenyl, $C_2-C_6$ haloalkenyl, $C_2-C_6$ alkynyl, $C_3-C_6$ haloalkynyl, $C_2-C_6$ alkoxyalkyl, $C_2-C_6$ alkylthioalkyl, $C_1-C_6$ nitroalkyl, $C_2-C_6$ cyanoalkyl; $C_3-C_8$ alkoxycarbonylalkyl, $C_3-C_6$ cycloalkyl, $C_3-C_6$ halocycloalkyl; and phenyl and benzyl each optionally substituted with 1 to 3 substituents independently selected from W;

$R^{18}$ is phenyl optional substituted with 1 to 3 substituents independently selected from W;

W is selected from the group halogen, CN, $N(R^7)R^8$, $NO_2$, $C_1-C_2$ alkyl, $C_1-C_2$ haloalkyl, $C_1-C_2$ alkoxy, $C_1-C_2$ haloalkoxy, $C_1-C_2$ alkylthio, $C_1-C_2$ haloalkylthio, $C_1$-$C_2$ alkylsulfonyl and $C_1$-$C_2$ haloalkylsulfonyl;

v is 4 or 5;

m is 1 to 3;

n is 1 or 2; and q is 0, 1 or 2.

Preferred Compounds A are compounds wherein:

$R^1$ and $R^2$ are independently selected from the group halogen, $C_1$-$C_6$ haloalkyl and $C_1$-$C_6$ haloalkoxy;

$R^3$ is selected from the group $C_1$-$C_6$ alkyl; and phenyl optionally substituted with a substituent selected from halogen, $C_1$-$C_2$ haloalkyl and $C_1$-$C_2$ haloalkoxy;

$R^4$ and $R^5$ are H; and

X is O.

Compounds of this invention can exist as one or more stereoisomers. The various stereoisomers include enantiomers, diastereomers and geometric isomers. One skilled in the art will appreciate that one stereoisomer may be more active than the others and how to separate said stereoisomers. Accordingly, the present invention comprises racemic mixtures, individual stereoisomers, and optically active mixtures of compounds of Formula I.

In the above definitions, the term "alkyl", used either alone or in compound words such as "alkythio" or "haloalkyl", denotes straight chain or branched alkyl such as methyl, ethyl, n-propyl, isopropyl, and the different butyl, pentyl and hexyl isomers.

Alkoxy denotes methoxy, ethoxy, n-propyloxy, isopropyloxy and the various isomers of butoxy, pentoxy and hexyloxy.

Alkenyl denotes straight chain or branched alkenes such as vinyl, 1-propenyl, 2-propenyl, 3-propenyl and the different butenyl, pentenyl and hexenyl isomers.

Alkynyl denotes straight or branched alkynes such as ethynyl, 1-propynyl, 2-propynyl and the different butynyl, pentynyl and hexynyl isomers.

Alkylthio denotes methylthio, ethylthio, n-propylthio, isopropylthio and the different butylthio, pentylthio and hexylthio isomers.

The term "halogen", either alone or in compound words as "haloalkyl", denotes fluorine, chlorine, bromine or iodine. Further, when used in compound words such as "haloalkyl" said alkyl can be partially or fully substituted with halogen atoms, which can be the same or different. Examples of haloalkyl include $CH_2CHF_2$, $CF_2CF_3$ and $CH_2CHFCl$.

The total number of carbon atoms in a substituent group is indicated by the "$C_i$-$C_j$" prefix where i and j are numbers from 1 to 22. For example, $C_1$-$C_3$ alkyl designates methyl through propyl; and $C_2$ alkoxy designates $OCH_2CH_3$ and $C_3$ alkoxy designates $OCH_2CH_2CH_3$ and $OCH(CH_3)_2$.

When a compound is substituted with a substituent bearing a subscript that indicates the number of said substituents can exceel 1, said substituents (when they exceed 1) are independently selected from the group of defined substituents.

DETAILS OF THE INVENTION

Compounds of Formula I can be made by treatment of compounds of Formula II with an isocyanate or isothiocyanate of Formula III as shown in Scheme 1. The reaction can be carried out in many inert solvents at 0°-100° C. Preferably, the process is carried out at room temperature in tetrahydrofuran, ether, or dichloromethane. Often, when the reaction is done in ether, the compound of Formula I precipitates and can be directly purified and isolated by filtration.

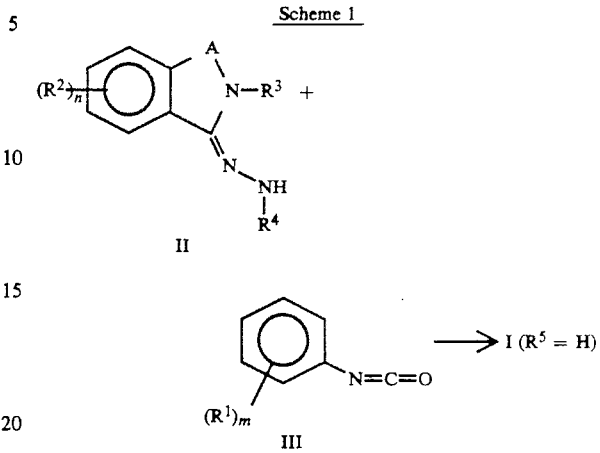

Scheme 1

As shown in Scheme 2, compounds of Formula I can also made by reaction of an activated salt of Formula IV with a hydrazine derivative of Formula V. This reaction can be carried out in a variety of solvents and temperatures. Depending of the reactivity of the salt IV, the reaction can be carried out from room temperature to 120° C. The reaction is best carried out in a solvent of high polarity. Lower alcohols and acetonitrile are very suitable for this process. In some cases, the reaction can also be carried out in basic solvents such as pyridine. In other cases, an added base such as triethylamine can also help the process.

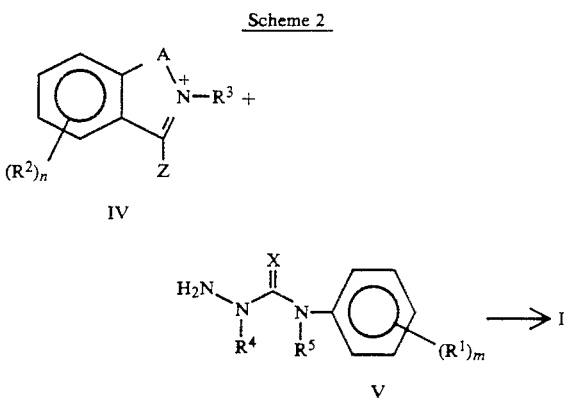

Scheme 2

Z = halogen, alkylthio, alkoxy

Compounds of Formula I can also be made by the reaction of compounds of Formula VI (where A =C(O), S(O)$_2$, or where $R^3$=H) with compounds of Formula V as represented in Scheme 3. The reaction is best carried out in solvents of high polarity such as lower alcohols or acetonitrile. The reaction is normally carried out at the reflux temperature of the solvent, but can be carried out at lower temperatures in certain cases. The compounds of Formula VI where A=C(O) and S(O)$_2$ are well known in the art and can be made from the appropriate saccharin or phthalimide derivative. (See for example: Köhler et. al., Chem. Ber., 100, 1073-1081 (1967)).

Scheme 3

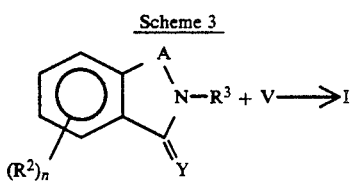

A = CO or SO₂ or R³ = H

Y = O, S

As shown in Scheme 4 compounds of Formula II can be made by the reaction of compounds of Formulae IV and VI with hydrazines of Formula VII. The reaction can be carried out in alcohols or other high polarity solvents. The temperature of the reaction can be widely varied with temperatures from room temperature to 100° C. being preferred. When hydrazine itself is used, care must be taken to use the hydrazine in excess or to carry out the addition in such a manner that the hydrazine is in excess during the reaction. This avoids the formation of azine from two moles of compounds of Formulae IV or VI.

Scheme 4

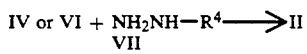

Compounds of Formula IV wherein R³ is alkyl or substituted alkyl can be made by the action of alkylating agents on compounds of Formula VI or VIII as depicted in Scheme 5. A review of the synthesis of salts from amides or thioamides can be found in Glushkov and Granik Advances in Heterocyclic Chemistry, Academic Press, New York, editors Katritsky and Boulton, Vol. 12, 185-212 (1970). Alkylation can be carried out with a variety of reagents which are highly reactive. Examples of these include sulfonates, triflates, oxonium salts, sulfates, and halides. The reaction is best carried out in inert solvents such as alkyl ketones, ethers, halogenated hydrocarbons and the like. In the case of alkyl halides, the reaction can be carried out without other solvents. Many compounds of Formula IV are known in the art. For example, see Kreher et. al. Zeitschrift fur Naturforschung, 44b, 1132-1148 (1989) for phthalimidines (A=CH₂); Fisher and Hamer, J. Chem. Soc., 1908, (1934) for isoquinolines (A=CH=CH); Tomita et. al., Chem. Pharm. Bull., 27, 2398-2404 (1979) for benzisoxazoles (A=O).

Scheme 5

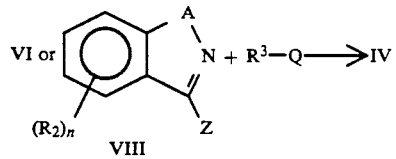

Z is halogen, thioalkyl, alkoxy
R³ = alkyl, substituted alkyl
Q = sulfate, triflate, halogen, etc.

Compounds of Formula VI are generally known in the art (See for example: Grigg et. al., J. Chem. Soc. Chem. Comm., 1183-1184, (1985) (A=CH2); Böshagen, Chem. Ber., 100, 954-956, (1967) (A=O); Davies et. al., J. Chem. Soc. Perkin 1, 180-184 (1978) (A=CH₂CH₂) Wachi, Chem. Pharm. Bull., 28, 465-471 (1980) (A=O-substituted carbon) or are commercially available especially when R³=H. The conversion of compounds of Formula VI (R³=H) to other compounds of Formula VI (R³=alkyl, substituted alkyl) when an amide linkage is present as shown in Scheme 6 is known. The alkylation can be carried out with alkyl halides or sulfonates in the presence of a base. The reaction is generally carried out in solvents inert to the presence of a base such as dimethylformamide or tetrahydrofuran. Depending on the group A, many different bases can be used including the alkali carbonates, alkali hydrides, or alkoxides. The temperature at which the process is carried out is not usually critical and can be carried out at room temperature.

Scheme 6

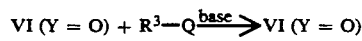

(R³ = H)         (R³ = alkyl, substituted alkyl)

Compounds of Formula VIII are also well known in the art. See Böshagen, Chem. Ber., 100, 3326-3330 (1967), (A=O); Gittos et. al. J. Chem. Soc. Perkin 1, 33-38 (1976) and references cited within (A=CH₂CH₂); Eloy and Deryckere, Helv. Chim. Acta, 52, 1755-1762 (1969) and references cited within (A=CH=CH); and Hennige et. al., Chem. Ber., 121, 243-252 (1988) (A=CH₂). Typically, as shown in Scheme 7, compounds of Formula VIII where Z is halogen can be made by treatment of the compound of Formula VI with a phosphorous oxyhalide in the presence or absence of an amine base as disclosed by Böshagen, Chem. Ber., 100, 3326-3330 (1967).

Scheme 7

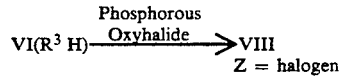

Z = halogen

Scheme 8 shows the synthesis of compounds of Formula VIII where Z is thioalkyl or alkoxy from the appropriate Compound VI by treatment with an activated alkylating agent. When VI is a thioamide, alkyl sulfate, sulfonates, oxonium salts and halides can be used for the conversion. For amides (VI), use of sulfates or oxonium salts is typically required for alkylation on oxygen. For this type of reaction, see Glushkov and Granik Advances in Heterocyclic Chemistry Academic Press, New York, editors Katritsky and Boulton, Vol. 12, 185-212 (1970).

Scheme 8

(Y = O,S)

EXAMPLE 1

2-(3,4-Dihydro-2-methyl-1(2H)-isoquinolinylidene)-N-[4-(trifluoromethyl)phenyl]-hydrazinecarboxamide The compound, 3,4-Dihydro-1-methylthioisoquinoline (J. Chem. Soc. Perkin 1, 33 (1976)), (2.0 g) was treated with methyl iodide (7 mL) and heated at reflux for 10 h. The cooled mixture was filtered and washed with cold acetone (2×10 mL). The solid (0.86 g) was treated with 4-trifluoromethylphenylsemicarbazide (0.7 g) in ethanol (10 mL) and was heated at reflux for 3 h. The mixture was cooled and diluted with water and treated with aqueous ammonium hydroxide (1.5 mL). The suspension was extracted with dichloromethane. The residue was subjected to column chromatography on silica gel in hexanes/ethyl acetate (2:1) to provide an off-white solid (0.6 g), mp 101°–104° C., $^1$H NMR (CDCl$_3$, 200 MHz) δ 8.4–7.2 (ArH and NH), 3.2 (CH$_2$N), 2.9 (CH$_2$), 2.8 (CH$_3$).

EXAMPLE 2

2-(2,3-Dihydro-2,2-dimethyl-4H-1,3-benzoxazin-4-yldine)-N-[4-(trifluoromethoxy)phenyl]-hydrazinecarboxamide A mixture of 1.77 g of 2,2-dimethyl-1,3-benzoxazin-4-one (prepared by the method of K. Wachi, et. al., Chem. Pharm. Bull., 28(2), 465–472, (1980)), 2.08 g of PCl$_5$, and 2 mL of POCl$_3$ was stirred for one hour at room temperature and for two hours at 50° C. Volatile material was removed by vacuum distillation. The residue was dissolved in 50 mL of acetonitrile, 2.35 g of 4-(4-trifluoromethoxy)phenylsemicarbazide was added, and the mixture was heated at reflux for several hours, until thin layer chromatographic analysis showed consumption of the intermediate imino chloride. The solvent was evaporated, and the residue was chromatographed on silica gel to isolate 0.60 g of a compound of this invention as a white solid, m.p. 155° C. $^1$H NMR (CDCl$_3$, 400 MHz); δ 1.48 (s, 3H), 1.61 (s, 3H), 6.2 (s, NH), 6.9 (m, 1H), 7.0 (m, 1H), 7.2 (m, 2H), 7.35 (m, 1H), 7.5 (m, 2H), 7.9 (m, 1H), 8.35 (s, NH), 9.8 (s, NH).

By the procedures described herein, the following compounds of Table 1 can be prepared. The compounds in Table 1, line 1 can be referred to as 1-1, 1-2, 1-3, 1-4 and 1-5 (as designated by line and column). All the other specific compounds covered in these Tables can be designated in an analogous fashion. The following abbreviations have been used in Table 1: Me=methyl, Et=ethyl, Pr=n-propyl, iPr=isopropyl, Ph=phenyl.

TABLE 1

| | | | Column Number | | |
|---|---|---|---|---|---|
| | 1 | 2 | 3 | 4 | 5 |
| 1  | A=O; R¹=CF₃; R³=CH₃; R²= | 5-F | 5-Cl | 5-CF₃ | 4-F | 4-Cl |
| 2  | A=O; R¹=OCF₃; R³=CH₃; R²= | 5-F | 5-Cl | 5-CF₃ | 4-F | 4-Cl |
| 3  | A=O; R¹=Br; R³=CH₃; R²= | 5-F | 5-Cl | 5-CF₃ | 4-F | 4-Cl |
| 4  | A=O; R¹=CF₃; R³=Et; R²= | 5-F | 5-Cl | 5-CF₃ | 4-F | 4-Cl |
| 5  | A=O; R¹=OCF₃; R³=Et; R²= | 5-F | 5-Cl | 5-CF₃ | 4-F | 4-Cl |
| 6  | A=O; R¹=Br; R³=Et; R²= | 5-F | 5-Cl | 5-CF₃ | 4-F | 4-Cl |
| 7  | A=O; R¹=CF₃; R³=nPr; R²= | 5-F | 5-Cl | 5-CF₃ | 4-F | 4-Cl |
| 8  | A=O; R¹=OCF₃; R³=nPr; R²= | 5-F | 5-Cl | 5-CF₃ | 4-F | 4-Cl |
| 9  | A=O; R¹=Br; R³=nPr; R²= | 5-F | 5-Cl | 5-CF₃ | 4-F | 4-Cl |
| 10 | A=O; R¹=CF₃; R³=iPr; R²= | 5-F | 5-Cl | 5-CF₃ | 4-F | 4-Cl |
| 11 | A=O; R¹=OCF₃; R³=iPr; R²= | 5-F | 5-Cl | 5-CF₃ | 4-F | 4-Cl |
| 12 | A=O; R¹=Br; R³=iPr; R²= | 5-F | 5-Cl | 5-CF₃ | 4-F | 4-Cl |
| 13 | A=O; R¹=CF₃; R³=Ph; R²= | 5-F | 5-Cl | 5-CF₃ | 4-F | 4-Cl |
| 14 | A=O; R¹=OCF₃; R³=Ph; R²= | 5-F | 5-Cl | 5-CF₃ | 4-F | 4-Cl |
| 15 | A=O; R¹=Br; R³=Ph; R²= | 5-F | 5-Cl | 5-CF₃ | 4-F | 4-Cl |
| 16 | A=O; R¹=CF₃; R³=4-F—Ph; R²= | 5-F | 5-Cl | 5-CF₃ | 4-F | 4-Cl |
| 17 | A=O; R¹=OCF₃; R³=4-F—Ph; R²= | 5-F | 5-Cl | 5-CF₃ | 4-F | 4-Cl |
| 18 | A=O; R¹=Br; R³=4-F—Ph; R²= | 5-F | 5-Cl | 5-CF₃ | 4-F | 4-Cl |
| 19 | A=O; R¹=CF₃; R³=4-Cl—Ph; R²= | 5-F | 5-Cl | 5-CF₃ | 4-F | 4-Cl |
| 20 | A=O; R¹=OCF₃; R³=4-Cl—Ph; R²= | 5-F | 5-Cl | 5-CF₃ | 4-F | 4-Cl |
| 21 | A=O; R¹=Br; R³=4-Cl—Ph; R²= | 5-F | 5-Cl | 5-CF₃ | 4-F | 4-Cl |
| 22 | A=CH₂; R¹=CF₃; R³=Me; R²= | 5-F | 5-Cl | 5-CF₃ | 4-F | 4-Cl |
| 23 | A=CH₂; R¹=OCF₃; R³=Me; R²= | 5-F | 5-Cl | 5-CF₃ | 4-F | 4-Cl |
| 24 | A=CH₂; R¹=CF₃; R³=Et; R²= | 5-F | 5-Cl | 5-CF₃ | 4-F | 4-Cl |
| 25 | A=CH₂; R¹=OCF₃; R³=Et; R²= | 5-F | 5-Cl | 5-CF₃ | 4-F | 4-Cl |
| 26 | A=CH₂; R¹=CF₃; R³=Pr; R²= | 5-F | 5-Cl | 5-CF₃ | 4-F | 4-Cl |
| 27 | A=CH₂; R¹=OCF₃; R³=Pr; R²= | 5-F | 5-Cl | 5-CF₃ | 4-F | 4-Cl |
| 28 | A=CH₂; R¹=Br; R³=Pr; R²= | 5-F | 5-Cl | 5-CF₃ | 4-F | 4-Cl |
| 29 | A=CH₂; R¹=CF₃; R³=iPr; R²= | 5-F | 5-Cl | 5-CF₃ | 4-F | 4-Cl |
| 30 | A=CH₂; R¹=OCF₃; R³=iPr; R²= | 5-F | 5-Cl | 5-CF₃ | 4-F | 4-Cl |
| 31 | A=CH₂; R¹=CF₃; R³=Ph; R²= | 5-F | 5-Cl | 5-CF₃ | 4-F | 4-Cl |
| 32 | A=CH₂; R¹=OCF₃; R³=Ph; R²= | 5-F | 5-Cl | 5-CF₃ | 4-F | 4-Cl |
| 33 | A=SO₂; R¹=CF₃; R³=CH₃; R²= | 5-F | 5-Cl | 5-CF₃ | 4-F | 4-Cl |
| 34 | A=SO₂; R¹=OCF₃; R³=CH₃; R²= | 5-F | 5-Cl | 4-CF₃ | 4-F | 4-Cl |
| 35 | A=SO₂; R¹=Br; R³=CH₃; R²= | 5-F | 5-Cl | 4-CF₃ | 4-F | 4-Cl |
| 36 | A=SO₂; R¹=CF₃; R³=Et; R²= | 5-F | 5-Cl | 4-CF₃ | 4-F | 4-Cl |
| 37 | A=SO₂; R¹=OCF₃; R³=Et; R²= | 5-F | 5-Cl | 4-CF₃ | 4-F | 4-Cl |
| 38 | A=SO₂; R¹=Br; R³=Et; R²= | 5-F | 5-Cl | 4-CF₃ | 4-F | 4-Cl |

TABLE 1-continued

| | | | | | |
|---|---|---|---|---|---|
| 39 | A=SO₂; R¹=CF₃; R³=nPr; R²= | 5-F | 5-Cl | 4-CF₃ | 4-F | 4-Cl |
| 40 | A=SO₂; R¹=OCF₃; R³=nPr; R²= | 5-F | 5-Cl | 4-CF₃ | 4-F | 4-Cl |
| 41 | A=SO₂; R¹=Br; R³=nPr; R²= | 5-F | 5-Cl | 4-CF₃ | 4-F | 4-Cl |
| 42 | A=SO₂; R¹=CF₃; R³=iPr; R²= | 5-F | 5-Cl | 4-CF₃ | 4-F | 4-Cl |
| 43 | A=SO₂; R¹=OCF₃; R³=iPr; R²= | 5-F | 5-Cl | 4-CF₃ | 4-F | 4-Cl |
| 44 | A=SO₂; R¹=Br; R³=iPr; R²= | 5-F | 5-Cl | 4-CF₃ | 4-F | 4-Cl |
| 45 | A=SO₂; R¹=CF₃; R³=Ph; R²= | 5-F | 5-Cl | 4-CF₃ | 4-F | 4-Cl |
| 46 | A=SO₂; R¹=OCF₃; R³=Ph; R²= | 5-F | 5-Cl | 4-CF₃ | 4-F | 4-Cl |
| 47 | A=SO₂; R¹=Br; R³=Ph; R²= | 5-F | 5-Cl | 4-CF₃ | 4-F | 4-Cl |
| 48 | A=SO₂; R¹=CF₃; R³=4-F—Ph; R²= | 5-F | 5-Cl | 4-CF₃ | 4-F | 4-Cl |
| 49 | A=SO₂; R¹=OCF₃; R³=4-F—Ph; R²= | 5-F | 5-Cl | 4-CF₃ | 4-F | 4-Cl |
| 50 | A=SO₂; R¹=Br; R³=4-F—Ph; R²= | 5-F | 5-Cl | 4-CF₃ | 4-F | 4-Cl |
| 51 | A=SO₂; R¹=CF₃; R³=4-Cl—Ph; R²= | 5-F | 5-Cl | 4-CF₃ | 4-F | 4-Cl |
| 52 | A=SO₂; R¹=OCF₃; R³=4-Cl—Ph; R²= | 5-F | 5-Cl | 4-CF₃ | 4-F | 4-Cl |
| 53 | A=SO₂; R¹=Br; R³=4-Cl—Ph; R²= | 5-F | 5-Cl | 4-CF₃ | 4-F | 4-Cl |
| 54 | A=S; R¹=CF₃; R³=Me; R²= | 5-F | 5-Cl | 4-CF₃ | 4-F | 4-Cl |
| 55 | A=S; R¹=OCF₃; R³=Me; R²= | 5-F | 5-Cl | 4-CF₃ | 4-F | 4-Cl |
| 56 | A=S; R¹=CF₃; R³=Et; R²= | 5-F | 5-Cl | 4-CF₃ | 4-F | 4-Cl |
| 57 | A=S; R¹=OCF₃; R³=Et; R²= | 5-F | 5-Cl | 4-CF₃ | 4-F | 4-Cl |
| 58 | A=S; R¹=CF₃; R³=Pr; R²= | 5-F | 5-Cl | 4-CF₃ | 4-F | 4-Cl |
| 59 | A=S; R¹=OCF₃; R³=Pr; R²= | 5-F | 5-Cl | 4-CF₃ | 4-F | 4-Cl |
| 60 | A=S; R¹=Br; R³=Pr; R²= | 5-F | 5-Cl | 4-CF₃ | 4-F | 4-Cl |
| 61 | A=S; R¹=CF₃; R³=iPr; R²= | 5-F | 5-Cl | 4-CF₃ | 4-F | 4-Cl |
| 62 | A=S; R¹=OCF₃; R³=iPr; R²= | 5-F | 5-Cl | 4-CF₃ | 4-F | 4-Cl |
| 63 | A=S; R¹=CF₃; R³=Ph; R²= | 5-F | 5-Cl | 4-CF₃ | 4-F | 4-Cl |
| 64 | A=S; R¹=OCF₃; R³=Ph; R²= | 5-F | 5-Cl | 4-CF₃ | 4-F | 4-Cl |
| 65 | A=CH₂CH₂; R¹=CF₃; R³=CH₃; R²= | 5-F | 5-Cl | 4-CF₃ | 4-F | 4-Cl |
| 66 | A=CH₂CH₂; R¹=OCF₃; R³=CH₃; R²= | 5-F | 5-Cl | 4-CF₃ | 4-F | 4-Cl |
| 67 | A=CH₂CH₂; R¹=Br; R³=CH; R²= | 5-F | 5-Cl | 4-CF₃ | 4-F | 4-Cl |
| 68 | A=CH₂CH₂; R¹=CF₃; R³=Et; R²= | 5-F | 5-Cl | 4-CF₃ | 4-F | 4-Cl |
| 69 | A=CH₂CH₂; R¹=OCF₃; R³=Et; R²= | 5-F | 5-Cl | 4-CF₃ | 4-F | 4-Cl |
| 70 | A=CH₂CH₂; R¹=Br; R³=Et; R²= | 5-F | 5-Cl | 4-CF₃ | 4-F | 4-Cl |
| 71 | A=CH₂CH₂; R¹=CF₃; R³=nPr; R²= | 5-F | 5-Cl | 4-CF₃ | 4-F | 4-Cl |
| 72 | A=CH₂CH₂; R¹=OCF₃; R³=nPr; R²= | 5-F | 5-Cl | 4-CF₃ | 4-F | 4-Cl |
| 73 | A=CH₂CH₂; R¹=Br; R³=nPr; R²= | 5-F | 5-Cl | 4-CF₃ | 4-F | 4-Cl |
| 74 | A=CH₂CH₂; R¹=OCF₃; R³=iPr; R²= | 5-F | 5-Cl | 4-CF₃ | 4-F | 4-Cl |
| 75 | A=CH₂CH₂; R¹=Br; R³=iPr; R²= | 5-F | 5-Cl | 4-CF₃ | 4-F | 4-Cl |
| 76 | A=CH₂CH₂; R¹=CF₃; R³=Ph; R²= | 5-F | 5-Cl | 4-CF₃ | 4-F | 4-Cl |
| 77 | A=CH₂CH₂; R¹=OCF₃; R³=Ph; R²= | 5-F | 5-Cl | 4-CF₃ | 4-F | 4-Cl |
| 78 | A=CH₂CH₂; R¹=Br; R³=Ph; R²= | 5-F | 5-Cl | 4-CF₃ | 4-F | 4-Cl |
| 79 | A=CH₂CH₂; R¹=CF₃; R³=4-F—Ph; R²= | 5-F | 5-Cl | 4-CF₃ | 4-F | 4-Cl |
| 80 | A=CH₂CH₂; R¹=OCF₃; R³=4-F—Ph; R²= | 5-F | 5-Cl | 4-CF₃ | 4-F | 4-Cl |
| 81 | A=CH₂CH₂; R¹=Br; R³=4-F—Ph; R²= | 5-F | 5-Cl | 4-CF₃ | 4-F | 4-Cl |
| 82 | A=CH₂CH₂; R¹=CF₃; R³=4-Cl—Ph; R²= | 5-F | 5-Cl | 4-CF₃ | 4-F | 4-Cl |
| 83 | A=CH₂CH₂; R¹=OCF₃; R³=4-Cl—Ph; R²= | 5-F | 5-Cl | 4-CF₃ | 4-F | 4-Cl |
| 84 | A=CH₂CH₂; R¹=Br; R³=4-Cl—Ph; R²= | 5-F | 5-Cl | 4-CF₃ | 4-F | 4-Cl |
| 85 | A=OCH₂; R¹=CF₃; R³=Me; R²= | 5-F | 5-Cl | 4-CF₃ | 4-F | 4-Cl |
| 86 | A=OCH₂; R¹=OCF₃; R³=Me; R²= | 5-F | 5-Cl | 4-CF₃ | 4-F | 4-Cl |
| 87 | A=OCH₂; R¹=CF₃; R³=Et; R²= | 5-F | 5-Cl | 4-CF₃ | 4-F | 4-Cl |
| 88 | A=OCH₂; R¹=OCF₃; R³=Et; R²= | 5-F | 5-Cl | 4-CF₃ | 4-F | 4-Cl |
| 89 | A=OCH₂; R¹=CF₃; R³=Pr; R²= | 5-F | 5-Cl | 4-CF₃ | 4-F | 4-Cl |
| 90 | A=OCH₂; R¹=OCF₃; R³=Pr; R²= | 5-F | 5-Cl | 4-CF₃ | 4-F | 4-Cl |
| 91 | A=OCH₂; R¹=OCF₃; R³=Pr; R²= | 5-F | 5-Cl | 4-CF₃ | 4-F | 4-Cl |

TABLE 1-continued

| | | | | |
|---|---|---|---|---|
| 92 | A=OCH; R$^1$=Br; R$^3$=Pr; R$^2$= | 5-F | 5-Cl | 4-CF$_3$ | 4-F | 4-Cl |
| 93 | A=OCH; R$^1$=CF$_3$; R$^3$=iPr; R$^2$= | 5-F | 5-Cl | 4-CF$_3$ | 4-F | 4-Cl |
| 94 | A=OCH; R$^1$=OCF$_3$; R$^3$=iPr; R$^2$= | 5-F | 5-Cl | 4-CF$_3$ | 4-F | 4-Cl |
| 95 | A=OCH; R$^1$=CF$_3$; R$^3$=Ph; R$^2$= | 5-F | 5-Cl | 4-CF$_3$ | 4-F | 4-Cl |
| 96 | A=OCH; R$^1$=OCF$_3$; R$^3$=Ph; R$^2$= | 5-F | 5-Cl | 4-CF$_3$ | 4-F | 4-Cl |
| 97 | A=CH=CH; R$^1$=CF$_3$; R$^3$=CH$_3$; R$^2$= | 5-F | 5-Cl | 4-CF$_3$ | 4-F | 4-Cl |
| 98 | A=CH=CH; R$^1$=OCF$_3$; R$^3$=CH$_3$; R$^2$= | 5-F | 5-Cl | 4-CF$_3$ | 4-F | 4-Cl |
| 99 | A=CH=CH; R$^1$=Br; R$^3$=CH$_3$; R$^2$= | 5-F | 5-Cl | 4-CF$_3$ | 4-F | 4-Cl |
| 100 | A=CH=CH; R$^1$=CF$_3$; R$^3$=Et; R$^2$= | 5-F | 5-Cl | 4-CF$_3$ | 4-F | 4-Cl |
| 101 | A=CH=CH; R$^1$=OCF$_3$; R$^3$=Et; R$^2$= | 5-F | 5-Cl | 4-CF$_3$ | 4-F | 4-Cl |
| 102 | A=CH=CH; R$^1$=Br; R$^3$=Et; R$^2$= | 5-F | 5-Cl | 4-CF$_3$ | 4-F | 4-Cl |
| 103 | A=CH=CH; R$^1$=CF$_3$; R$^3$=nPr; R$^2$= | 5-F | 5-Cl | 4-CF$_3$ | 4-F | 4-Cl |
| 104 | A=CH=CH; R$^1$=OCF$_3$; R$^3$=nPr; R$^2$= | 5-F | 5-Cl | 4-CF$_3$ | 4-F | 4-Cl |
| 105 | A=CH=CH; R$^1$=Br; R$^3$=nPr; R$^2$= | 5-F | 5-Cl | 4-CF$_3$ | 4-F | 4-Cl |
| 106 | A=CH=CH; R$^1$=CF$_3$; R$^3$=iPr; R$^2$= | 5-F | 5-Cl | 4-CF$_3$ | 4-F | 4-Cl |
| 107 | A=CH=CH; R$^1$=OCF$_3$; R$^3$=iPr; R$^2$= | 5-F | 5-Cl | 4-CF$_3$ | 4-F | 4-Cl |
| 108 | A=CH=CH; R$^1$=Br; R$^3$=iPr; R$^2$= | 5-F | 5-Cl | 4-CF$_3$ | 4-F | 4-Cl |
| 109 | A=CH=CH; R$^1$=CF$_3$; R$^3$=Ph; R$^2$= | 5-F | 5-Cl | 4-CF$_3$ | 4-F | 4-Cl |
| 110 | A=CH=CH; R$^1$=OCF$_3$; R$^3$=Ph; R$^2$= | 5-F | 5-Cl | 4-CF$_3$ | 4-F | 4-Cl |
| 111 | A=CH=CH; R$^1$=Br; R$^3$=Ph; R$^2$= | 5-F | 5-Cl | 4-CF$_3$ | 4-F | 4-Cl |
| 112 | A=CH=CH; R$^1$=CF$_3$; R$^3$=4-F—Ph; R$^2$= | 5-F | 5-Cl | 4-CF$_3$ | 4-F | 4-Cl |
| 113 | A=CH=CH; R$^1$=OCF$_3$; R$^3$=4-F—Ph; R$^2$= | 5-F | 5-Cl | 4-CF$_3$ | 4-F | 4-Cl |
| 114 | A=CH=CH; R$^1$=Br; R$^3$=4-F—Ph; R$^2$= | 5-F | 5-Cl | 4-CF$_3$ | 4-F | 4-Cl |
| 115 | A=CH=CH; R$^1$=CF$_3$; R$^3$=4-Cl—Ph; R$^2$= | 5-F | 5-Cl | 4-CF$_3$ | 4-F | 4-Cl |
| 116 | A=CH=CH; R$^1$=OCF$_3$; R$^3$=4-Cl—Ph; R$^2$= | 5-F | 5-Cl | 4-CF$_3$ | 4-F | 4-Cl |
| 117 | A=CH=CH; R$^1$=Br; R$^3$=4-Cl—Ph; R$^2$= | 5-F | 5-Cl | 4-CF$_3$ | 4-F | 4-Cl |
| 118 | A=SCH$_2$; R$^1$=CF$_3$; R$^3$=Me; R$^2$= | 5-F | 5-Cl | 4-CF$_3$ | 4-F | 4-Cl |
| 119 | A=SCH$_2$; R$^1$=OCF$_3$; R$^3$=Me; R$^2$= | 5-F | 5-Cl | 4-CF$_3$ | 4-F | 4-Cl |
| 120 | A=SCH$_2$; R$^1$=CF$_3$; R$^3$=Et; R$^2$= | 5-F | 5-Cl | 4-CF$_3$ | 4-F | 4-Cl |
| 121 | A=SCH$_2$; R$^1$=OCF$_3$; R$^3$=Et; R$^2$= | 5-F | 5-Cl | 4-CF$_3$ | 4-F | 4-Cl |
| 122 | A=SCH$_2$; R$^1$=CF$_3$; R$^3$=Pr; R$^2$= | 5-F | 5-Cl | 4-CF$_3$ | 4-F | 4-Cl |
| 123 | A=SCH$_2$; R$^1$=OCF$_3$; R$^3$=Pr; R$^2$= | 5-F | 5-Cl | 4-CF$_3$ | 4-F | 4-Cl |
| 124 | A=SCH$_2$; R$^1$=Br; R$^3$=Pr; R$^2$= | 5-F | 5-Cl | 4-CF$_3$ | 4-F | 4-Cl |
| 125 | A=SCH$_2$; R$^1$=CF$_3$; R$^3$=iPr; R$^2$= | 5-F | 5-Cl | 4-CF$_3$ | 4-F | 4-Cl |
| 126 | A=SCH$_2$; R$^1$=OCF$_3$; R$^3$=iPr; R$^2$= | 5-F | 5-Cl | 4-CF$_3$ | 4-F | 4-Cl |
| 127 | A=SCH$_2$; R$^1$=CF$_3$; R$^3$=Ph; R$^2$= | 5-F | 5-Cl | 4-CF$_3$ | 4-F | 4-Cl |
| 128 | A=SCH$_2$; R$^1$=OCF$_3$; R$^3$=Ph; R$^2$= | 5-F | 5-Cl | 4-CF$_3$ | 4-F | 4-Cl |
| 129 | A=NMe; R$^1$=CF$_3$; R$^3$=CH$_3$; R$^2$= | 5-F | 5-Cl | 4-CF$_3$ | 4-F | 4-Cl |
| 130 | A=NMe; R$^1$=OCF$_3$; R$^3$=CH$_3$; R$^2$= | 5-F | 5-Cl | 4-CF$_3$ | 4-F | 4-Cl |
| 131 | A=NMe; R$^1$=Br; R$^3$=CH$_3$; R$^2$= | 5-F | 5-Cl | 4-CF$_3$ | 4-F | 4-Cl |
| 132 | A=NMe; R$^1$=CF$_3$; R$^3$=Et; R$^2$= | 5-F | 5-Cl | 4-CF$_3$ | 4-F | 4-Cl |
| 133 | A=NMe; R$^1$=OCF$_3$; R$^3$=Et; R$^2$= | 5-F | 5-Cl | 4-CF$_3$ | 4-F | 4-Cl |
| 134 | A=NMe; R$^1$=Br; R$^3$=Et; R$^2$= | 5-F | 5-Cl | 4-CF$_3$ | 4-F | 4-Cl |
| 135 | A=NMe; R$^1$=CF$_3$; R$^3$=nPr; R$^2$= | 5-F | 5-Cl | 4-CF$_3$ | 4-F | 4-Cl |
| 136 | A=NMe; R$^1$=OCF$_3$; R$^3$=nPr; R$^2$= | 5-F | 5-Cl | 4-CF$_3$ | 4-F | 4-Cl |
| 137 | A=NMe; R$^1$=Br; R$^3$=nPr; R$^2$= | 5-F | 5-Cl | 4-CF$_3$ | 4-F | 4-Cl |
| 138 | A=NMe; R$^1$=CF$_3$; R$^3$=iPr; R$^2$= | 5-F | 5-Cl | 5-CF$_3$ | 4-F | 4-Cl |
| 139 | A=NMe; R$^1$=OCF$_3$; R$^3$=iPr; R$^2$= | 5-F | 5-Cl | 5-CF$_3$ | 4-F | 4-Cl |
| 140 | A=NMe; R$^1$=Br; R$^3$=iPr; R$^2$= | 5-F | 5-Cl | 5-CF$_3$ | 4-F | 4-Cl |
| 141 | A=NMe; R$^1$=CF$_3$; R$^3$=Ph; R$^2$= | 5-F | 5-Cl | 5-CF$_3$ | 4-F | 4-Cl |
| 142 | A=NMe; R$^1$=OCF$_3$; R$^3$=Ph; R$^2$= | 5-F | 5-Cl | 5-CF$_3$ | 4-F | 4-Cl |
| 143 | A=NMe; R$^1$=Br; R$^3$=Ph; R$^2$= | 5-F | 5-Cl | 5-CF$_3$ | 4-F | 4-Cl |
| 144 | A=NMe; R$^1$=CF$_3$; R$^3$=4-F—Ph; R$^2$= | 5-F | 5-Cl | 5-CF$_3$ | 4-F | 4-Cl |

| # | | 5-F | 5-Cl | | 4-Cl |
|---|---|---|---|---|---|
| 145 | A=NMe; R¹=OCF₃; R³=4-F—Ph; R²= | 5-F | 5-Cl | 5-CF₃ | 4-F | 4-Cl |
| 146 | A=NMe; R¹=Br; R³=4-F—Ph; R²= | 5-F | 5-Cl | 5-CF₃ | 4-F | 4-Cl |
| 147 | A=NMe; R¹=CF₃; R³=4-Cl—Ph; R²= | 5-F | 5-Cl | 5-CF₃ | 4-F | 4-Cl |
| 148 | A=NMe; R¹=OCF₃; R³=4-Cl—Ph; R²= | 5-F | 5-Cl | 5-CF₃ | 4-F | 4-Cl |
| 149 | A=NMe; R¹=Br; R³=4-Cl—Ph; R²= | 5-F | 5-Cl | 5-CF₃ | 4-F | 4-Cl |
| 150 | A=CO; R¹=CF₃; R³=Me; R²= | 5-F | 5-Cl | 5-CF₃ | 4-F | 4-Cl |
| 151 | A=CO; R¹=OCF₃; R³=Me; R²= | 5-F | 5-Cl | 5-CF₃ | 4-F | 4-Cl |
| 152 | A=CO; R¹=CF₃; R³=Et; R²= | 5-F | 5-Cl | 5-CF₃ | 4-F | 4-Cl |
| 153 | A=CO; R¹=OCF₃; R³=Et; R²= | 5-F | 5-Cl | 5-CF₃ | 4-F | 4-Cl |
| 154 | A=CO; R¹=CF₃; R³=Pr; R²= | 5-F | 5-Cl | 5-CF₃ | 4-F | 4-Cl |
| 155 | A=CO; R¹=OCF₃; R³=Pr; R²= | 5-F | 5-Cl | 5-CF₃ | 4-F | 4-Cl |
| 156 | A=CO; R¹=Br; R³=Pr; R²= | 5-F | 5-Cl | 5-CF₃ | 4-F | 4-Cl |
| 157 | A=CO; R¹=CF₃; R³=iPr; R²= | 5-F | 5-Cl | 5-CF₃ | 4-F | 4-Cl |
| 158 | A=CO; R¹=OCF₃; R³=iPr; R²= | 5-F | 5-Cl | 5-CF₃ | 4-F | 4-Cl |
| 159 | A=CO; R¹=CF₃; R³=Ph; R²= | 5-F | 5-Cl | 5-CF₃ | 4-F | 4-Cl |
| 160 | A=CO; R¹=OCF₃; R³=Ph; R²= | 5-F | 5-Cl | 5-CF₃ | 4-F | 4-Cl |
| 161 | A=CH₂O; R¹=CF₃; R³=CH₃; R²= | 5-F | 5-Cl | 4-CF₃ | 4-F | 4-Cl |
| 161 | A=CH₂O; R¹=OCF₃; R³=CH₃; R²= | 5-F | 5-Cl | 4-CF₃ | 4-F | 4-Cl |
| 162 | A=CH₂O; R¹=Br; R³=CH₃; R²= | 5-F | 5-Cl | 4-CF₃ | 4-F | 4-Cl |
| 164 | A=CH₂O; R¹=CF₃; R³=Et; R²= | 5-F | 5-Cl | 4-CF₃ | 4-F | 4-Cl |
| 165 | A=CH₂O; R¹=OCF₃; R³=Et; R²= | 5-F | 5-Cl | 4-CF₃ | 4-F | 4-Cl |
| 166 | A=CH₂O; R¹=Br; R³=Et; R²= | 5-F | 5-Cl | 4-CF₃ | 4-F | 4-Cl |
| 167 | A=CH₂O; R¹=CF₃; R³=nPr; R²= | 5-F | 5-Cl | 4-CF₃ | 4-F | 4-Cl |
| 168 | A=CH₂O; R¹=OCF₃; R³=nPr; R²= | 5-F | 5-Cl | 4-CF₃ | 4-F | 4-Cl |
| 169 | A=CH₂O; R¹=Br; R³=nPr; R²= | 5-F | 5-Cl | 4-CF₃ | 4-F | 4-Cl |
| 170 | A=CH₂O; R¹=CF₃; R³=iPr; R²= | 5-F | 5-Cl | 4-CF₃ | 4-F | 4-Cl |
| 171 | A=CH₂O; R¹=OCF₃; R³=iPr; R²= | 5-F | 5-Cl | 4-CF₃ | 4-F | 4-Cl |
| 172 | A=CH₂O; R¹=Br; R³=iPr; R²= | 5-F | 5-Cl | 4-CF₃ | 4-F | 4-Cl |
| 173 | A=CH₂O; R¹=CF₃; R³=Ph; R²= | 5-F | 5-Cl | 4-CF₃ | 4-F | 4-Cl |
| 174 | A=CH₂O; R¹=OCF₃; R³=Ph; R²= | 5-F | 5-Cl | 4-CF₃ | 4-F | 4-Cl |
| 175 | A=CH₂O; R¹=Br; R³=Ph; R²= | 5-F | 5-Cl | 4-CF₃ | 4-F | 4-Cl |
| 176 | A=CH₂O; R¹=CF₃; R³=4-F—Ph; R²= | 5-F | 5-Cl | 4-CF₃ | 4-F | 4-Cl |
| 177 | A=CH₂O; R¹=OCF₃; R³=4-F—Ph; R²= | 5-F | 5-Cl | 4-CF₃ | 4-F | 4-Cl |
| 178 | A=CH₂O; R¹=Br; R³=4-F—Ph; R²= | 5-F | 5-Cl | 4-CF₃ | 4-F | 4-Cl |
| 179 | A=CH₂O; R¹=CF₃; R³=4-Cl—Ph; R²= | 5-F | 5-Cl | 4-CF₃ | 4-F | 4-Cl |
| 180 | A=CH₂O; R¹=OCF₃; R³=4-Cl—Ph; R²= | 5-F | 5-Cl | 4-CF₃ | 4-F | 4-Cl |
| 181 | A=CH₂O; R¹=Br; R³=4-Cl—Ph; R²= | 5-F | 5-Cl | 4-CF₃ | 4-F | 4-Cl |
| 182 | A=CH₂S; R¹=CF₃; R³=Me; R²= | 5-F | 5-Cl | 4-CF₃ | 4-F | 4-Cl |
| 183 | A=CH₂S; R¹=OCF₃; R³=Me; R²= | 5-F | 5-Cl | 4-CF₃ | 4-F | 4-Cl |
| 184 | A=CH₂S; R¹=CF₃; R³=Et; R²= | 5-F | 5-Cl | 4-CF₃ | 4-F | 4-Cl |
| 185 | A=CH₂S; R¹=OCF₃; R³=Et; R²= | 5-F | 5-Cl | 4-CF₃ | 4-F | 4-Cl |
| 186 | A=CH₂S; R¹=CF₃; R³=Pr; R²= | 5-F | 5-Cl | 4-CF₃ | 4-F | 4-Cl |
| 187 | A=CH₂S; R¹=OCF₃; R³=Pr; R²= | 5-F | 5-Cl | 4-CF₃ | 4-F | 4-Cl |
| 188 | A=CH₂S; R¹=CF₃; R³=iPr; R²= | 5-F | 5-Cl | 4-CF₃ | 4-F | 4-Cl |
| 189 | A=CH₂S; R¹=OCF₃; R³=iPr; R²= | 5-F | 5-Cl | 4-CF₃ | 4-F | 4-Cl |
| 190 | A=CH₂S; R¹=CF₃; R³=Ph; R²= | 5-F | 5-Cl | 4-CF₃ | 4-F | 4-Cl |
| 191 | A=CH₂S; R¹=OCF₃; R³=Ph; R²= | 5-F | 5-Cl | 4-CF₃ | 4-F | 4-Cl |
| 192 | A=CH₂S; R¹=Br; R³=Ph; R²= | 5-F | 5-Cl | 4-CF₃ | 4-F | 4-Cl |
| 193 | A=OCMe₂; R¹=CF₃; R³=H; R²= | 5-F | 4-Cl | 4-CF₃ | 4-F | 4-Cl |
| 194 | A=OCMe₂; R¹=OCF₃; R³=H; R²= | 5-F | 4-Cl | 4-CF₃ | 4-F | 4-Cl |
| 195 | A=OCMe₂; R¹=Br; R³=H; R²= | 5-F | 4-Cl | 4-CF₃ | 4-F | 4-Cl |
| 196 | A=OCHMe; R¹=CF₃; R³=H; R²= | 5-F | 4-Cl | 4-CF₃ | 4-F | 4-Cl |
| 197 | A=OCHMe; R¹=OCF₃; R³=H; R²= | 5-F | 4-Cl | 4-F | 4-F | 4-Cl |
| 198 | A=OCHMe; R¹=Br; R³=H; R²= | 5-F | 4-Cl | 4-F | 4-F | 4-Cl |

-continued

| | | | | |
|---|---|---|---|---|
| 199 | A=OCHMe(Ph); R$^1$=CF$_3$; R$^3$=H; R$^2$= | 5-F | 4-CF$_3$ | 4-Cl |
| 200 | A=OCHMe(Ph); R$^1$=OCF$_3$; R$^3$=H; R$^2$= | 5-F | 4-CF$_3$ | 4-Cl |
| 201 | A=OCHMe(Ph); R$^1$=Br; R$^3$=H; R$^2$= | 5-F | 4-CF$_3$ | 4-Cl |
| 202 | A=OCHPh; R$^1$=CF$_3$; R$^3$=H; R$^2$= | 5-F | 4-CF$_3$ | 4-Cl |
| 203 | A=OCHPh; R$^1$=OCF$_3$; R$^3$=H; R$^2$= | 5-F | 4-CF$_3$ | 4-Cl |
| 204 | A=OCHPh; R$^1$=Br; R$^3$=H; R$^2$= | 5-F | 4-CF$_3$ | 4-Cl |
| 205 | A=SCMe$_2$; R$^1$=CF$_3$; R$^3$=H; R$^2$= | 5-F | 4-CF$_3$ | 4-Cl |
| 206 | A=SCMe$_2$; R$^1$=OCF$_3$; R$^3$=H; R$^2$= | 5-F | 4-CF$_3$ | 4-Cl |
| 207 | A=SCMe$_2$; R$^1$=Br; R$^3$=H; R$^2$= | 5-F | 4-CF$_3$ | 4-Cl |
| 208 | A=SCHMe; R$^1$=CF$_3$; R$^3$=H; R$^2$= | 5-F | 4-CF$_3$ | 4-Cl |
| 209 | A=SCHMe; R$^1$=OCF$_3$; R$^3$=H; R$^2$= | 5-F | 4-CF$_3$ | 4-Cl |
| 210 | A=SCHMe; R$^1$=Br; R$^3$=H; R$^2$= | 5-F | 4-CF$_3$ | 4-Cl |
| 211 | A=SCHPh; R$^1$=CF$_3$; R$^3$=H; R$^2$= | 5-F | 4-CF$_3$ | 4-Cl |
| 212 | A=SCHPh; R$^1$=OCF$_3$; R$^3$=H; R$^2$= | 5-F | 4-CF$_3$ | 4-Cl |
| 213 | A=SCHPh; R$^1$=Br; R$^3$=H; R$^2$= | 5-F | 4-CF$_3$ | 4-Cl |
| 214 | A=N(Me)CMe$_2$; R$^1$=CF$_3$; R$^3$=H; R$^2$= | 5-F | 4-CF$_3$ | 4-Cl |
| 215 | A=N(Me)CMe$_2$; R$^1$=OCF$_3$; R$^3$=H; R$^2$= | 5-F | 4-CF$_3$ | 4-Cl |
| 216 | A=N(Me)CMe$_2$; R$^1$=Br; R$^3$=H; R$^2$= | 5-F | 4-CF$_3$ | 4-Cl |
| 217 | A=N(Me)CHMe; R$^1$=CF$_3$; R$^3$=H; R$^2$= | 5-F | 4-CF$_3$ | 4-Cl |
| 218 | A=N(Me)CHMe; R$^1$=OCF$_3$; R$^3$=H; R$^2$= | 5-F | 4-CF$_3$ | 4-Cl |
| 219 | A=N(Me)CHMe; R$^1$=Br; R$^3$=H; R$^2$= | 5-F | 4-CF$_3$ | 4-Cl |
| 220 | A=N(Me)CHPh; R$^1$=CF$_3$; R$^3$=H; R$^2$= | 5-F | 4-CF$_3$ | 4-Cl |
| 221 | A=N(Me)CHPh; R$^1$=OCF$_3$; R$^3$=H; R$^2$= | 5-F | 4-CF$_3$ | 4-Cl |
| 222 | A=N(Me)CHPh; R$^1$=Br; R$^3$=H; R$^2$= | 5-F | 4-CF$_3$ | 4-Cl |

Formulation/Utility

Compounds of this invention will generally be used in formulation with an agriculturally suitable carrier comprising a liquid or solid diluent or an organic solvent. Use formulations include dusts, granules, baits, pellets, solutions, suspensions, emulsions, wettable powders, emulsifiable concentrates, dry flowables and the like, consistent with the physical properties of the active ingredient, mode of application and environmental factors such as soil type, moisture and temperature. Sprayable formulations can be extended in suitable media and used at spray volumes from about one to several hundred liters per hectare. High strength compositions are primarily used as intermediates for further formulation. The formulations will typically contain effective amounts of active ingredient, diluent and surfactant within the following approximate ranges which add up 100 weight percent.

|  | Weight Percent | | |
| --- | --- | --- | --- |
|  | Active Ingredient | Diluent | Surfactant |
| Wettable Powders | 25–90 | 0–74 | 1–10 |
| Oil Suspensions, Emulsions, Solutions, (including Emulsifiable Concentrates) | 5–50 | 40–95 | 0–15 |
| Dusts | 1–25 | 70–99 | 0–5 |
| Granules, Baits and Pellets | 0.01–99 | 5–99.99 | 0–15 |
| High Strength Compositions | 90–99 | 0–10 | 0–2 |

Typical solid diluents are described in Watkins, et al., Handbook of Insecticide Dust Diluents and Carriers, 2nd Ed., Dorland Books, Caldwell, N.J.. Typical liquid diluents and solvents are described in Marsden, Solvents Guide, 2nd Ed., Interscience, New York, 1950. McCutcheon's Detergents and Emulsifiers Annual, Allured Publ. Corp., Ridgewood, N.J., as well as Sisely and Wood, Encylcopedia of Surface Active Agents, Chemical Publ. Co., Inc., New York, 1964, list surfactants and recommended uses. All formulations can contain minor amounts of additives to reduce foam, caking, corrosion, microbiological growth, etc.

Solutions are prepared by simply mixing the ingredients. Fine solid compositions are made by blending and, usually, grinding as in a hammer mill or fluid energy mill. Water-dispersible granules can be produced by agglomerating a fine powder composition; see for example, Cross et al., Pesticide Formulations, Washington, D.C., 1988, pp 251–259. Suspensions are prepared by wet-milling; see, for example, U.S. Pat. No. 3,060,084. Granules and pellets can be made by spraying the active material upon preformed granular carriers or by agglomeration techniques. See Browning, "Agglomeration", Chemical Engineering, Dec. 4, 1967, pp 147–148, Perry's Chemical Engineer's Handbook, 4th Ed., McGraw-Hill, New York, 1963, pages 8–57 and following, and WO 91/13546. Pellets can be prepared as described in U.S. Pat. No. 4,172,714. Water-dispersible and water-soluble granules can also be prepared as taught in DE 3,246,493.

For further information regarding the art of formulation, see U.S. Pat. No. 3,235,361, Col. 6, line 16 through Col. 7, line 19 and Examples 10–41; U.S. Pat. No. 3,309,192, Col. 5, line 43 through Col. 7, line 62 and Examples 8, 12, 15, 39, 41, 52, 53, 58, 132, 138–140, 162–164, 166, 167 and 169–182; U.S. Pat. No. 2,891,855, Col. 3, line 66 through Col. 5, line 17 and Examples 1–4; Klingman, Weed Control as a Science, John Wiley and Sons, Inc., New York, 1961, pp 81–96; and Hance et al., Weed Control Handbook, 8th Ed., Blackwell Scientific Publications, Oxford, 1989.

In the following Examples, all percentages are by weight and all formulations are worked up in conventional ways. Compound numbers refer to compounds in Index Table A.

EXAMPLE A

| Wettable Powder | |
| --- | --- |
| Compound 1 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0% |

EXAMPLE B

| Granule | |
| --- | --- |
| Compound 1 | 10.0% |
| attapulgite granules (low volatile matter, 0.71/0.30 mm; U.S.S. No. 25–50 sieves) | 90.0% |

EXAMPLE C

| Extruded Pellet | |
| --- | --- |
| Compound 1 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0% |

EXAMPLE D

| Emulsifiable Concentrate | |
| --- | --- |
| Compound 1 | 20.0% |
| blend of oil soluble sulfonates and polyoxyethylene ethers | 10.0% |
| isophorone | 70.0% |

The compounds of this invention exhibit activity against a wide spectrum of foliar-feeding, fruit-feeding, seed-feeding, aquatic and soil-inhibiting arthropods (term includes nematodes) which are pests of growing and stored agronomic crops, forestry, greenhouse crops, ornamentals, nursery crops, stored food and fiber products, livestock, household, and public and animal health. Those skilled in the art will appreciate that not all compounds are equally effective against all pests. Nevertheless, all of the compounds of this invention display activity against pests that include: eggs, larvae and adults of the Order Lepidoptera; eggs, foliar-feeding, fruit-feeding, root-feeding, seed-feeding larvae and adults of the Order Coleoptera; eggs, immatures and adults of the Orders Hemiptera and Homoptera; eggs, larvae, nymphs and adults of the Order Acari; eggs, immatures and adults of the Orders Thysanoptera, Orthoptera and Dermaptera; eggs, immatures and adults of the Order Diptera; and eggs, juveniles and adults of the Phylum Nemata. The compounds of this invention are also active against pests of the Orders Hymenoptera, Isoptera, Phthiraptera, Siphonoptera, Blattaria, Thysanaura and Pscoptera; pests belonging to the Class Arachnida and Phylum Platyhelminthes. See WO 90/10623 and WO 92/00673 for more detailed pest descriptions.

Compounds of this invention can also be mixed with one or more other insecticides, fungicides, nematocides, bactericides, acaricides, semiochemicals, repellants, attractants, pheromones, feeding stimulants or other biologically active compounds to form a multi-component pesticide giving an even broader spectrum of agricultural protection. Examples of other agricultural protectants with which compounds of this invention can be formulated are: insecticides such as monocrotophos, carbofuran, tetrachlorvinphos, malathion, parathion—methyl, methonyl, chlordimeform, diazinon, deltamethrin, oxamyl, fenvalerate, esfenvalerate, permethrin, profenofos, sulprofos, triflumuron, diflubenzuron, methoprene, buprofezin, thiodicarb, acephate, azinphosmethyl, chlorpyrifos, dimethoate, fipronil, flufenprox, fonophos, isofenphos, methidathion, methamidophos, phosmet, phosphamidon, phosalone, pirimicarb, phorate, terbufos, trichlorfon, methoxychlor, bifenthrin, biphenate, cyfluthrin, fenpropathrin, fluvalinate, flucythrinate, tralomethrin, metaldehyde and rotenone; fungicides such as carbendazim, thiuram, dodine, maneb, chloroneb, benomyl, cymoxanil, fenpropidine, fenpropimorph, triadimefon, captan, thiophanate-methyl, thiabendazole, phosethyl-Al, chlorothalonil, dichloran, metalaxyl, captafol, iprodione, oxadixyl, vinclozolin, kasugamycin, myclobutanil, tebuconazole, difenoconazole, diniconazole, fluquinconazole, ipconazole, metconazole, penconazole, propiconazole, uniconzole, flutriafol, prochloraz, pyrifenox, fenarimol, triadimenol, diclobutrazol, copper oxychloride, furalaxyl, folpet, flusilazol, blasticidin S, diclomezine, edifenphos, isoprothiolane, iprobenfos, mepronil, neo-asozin, pencycuron, probenazole, pyroquilon, tricyclazole, validamycin, and flutolanil; nematocides such as aldoxycarb, fenamiphos and fosthietan; bactericides such as avermectin B, oxytetracyline, streptomycin and tribasic copper sulfate; acaricides such as binapacryl, oxythioquinox, chlorobenzilate, dicofol, dienochlor, cyhexatin, hexythiazox, amitraz, propargite, tebufenpyrad and fenbutatin oxide; and biological agents such as Bacillus thuringiensis and baculovirus.

In certain instances, combinations with other arthropodicides having a similiar spectrum of control but a different mode of action will be particularly advantageous for resistance management.

Arthropod pests are controlled and protection of agronomic crops, animal and human health is achieved by applying one or more of the compounds of this invention, in an effective amount, to the environment of the pests including the agronomic and/or nonagronomic locus of infestation, to the area to be protected, or directly on the pests to be controlled. A preferred method of application is by spraying. Alternatively, granular formulations of these compounds can be applied to the plant foliage or the soil. Other methods of application include direct and residual sprays, aerial sprays, systemic uptake, baits, eartags, boluses, foggers, fumigants, aerosols, and many others. The compounds can be incorporated into baits that are consumed by the arthropods or in devices such as traps and the like.

The compounds of this invention can be applied in their pure state, but most often application will be of a formulation comprising one or more compounds with suitable carriers, diluents, and surfactants and possibly in combination with a food depending on the contemplated end use. A preferred method of application involves spraying a water dispersion or refined oil solution of the compounds. Combinations with spray oils, spray oil concentrations, spreader stickers, adjuvants, and synergists and other solvents such as piperonyl butoxide often enhance compound efficacy.

The rate of application required for effective control will depend on such factors as the species of arthropod to be controlled, the pest's life cycle, life stage, its size, location, time of year, host crop or animal, feeding behavior, mating behavior, ambient moisture, temperature, and the like. Under normal circumstances, application rates of about 0.01 to 2 kg of active ingredient per hectare are sufficient to control pests in agronomic ecosystems, but as little as 0.001 kg/hectare may be sufficient or as much as 8 kg hectare may be required. For nonagronomic applications, effective use rates will range from about 1.0 to 50 mg/square meter but as little as 0.1 mg/square meter may be sufficient or as much as 150 mg/square meter may be required.

The following Tests demonstrate the control efficacy of compounds of this invention on specific pests. The pest control protection afforded by the compounds is not limited, however, to these species. See Index Table A for compound descriptions.

Index Table A

| Compound | A | $R^2$ | $R^1$ | $R^3$ | mp° C. |
|---|---|---|---|---|---|
| 1 | CH=CH | H | $CF_3$ | Me | 167–69 |
| 2 | CH=CH | H | $CF_3$ | Et | 150–52 |
| 3 | CH=CH | H | $CF_3$ | Allyl | 161–65 |
| 4 | CH=CH | H | $CF_3$ | Benzyl | 182–90 |
| 5 | CH=CH | 3-Cl | $CF_3$ | Et | 200–05 |
| 6 | CH=CH | H | $OCF_3$ | Et | 152–54 |
| 7 | CH=CH | 4-Cl | $OCF_3$ | Et | 153–54 |
| 8 | CH=CH | H | $OCF_3$ | n-Pr | 120–24 |
| 9 | CH=CH | H | $OCF_3$ | i-Pr | 159–61 |
| 10 | CH=CH | 4-Cl | $CF_3$ | Et | 174–76 |
| 11 | CH=CH | H | $CF_3$ | n-Pr | 169–71 |
| 12 | C(Cl)=CH | H | $OCF_3$ | Et | 171–72 |
| 13 | C(Cl)=CH | H | $CF_3$ | n-Pr | 204–05 |
| 14 | C(Cl)=CH | H | $OCF_3$ | n-Pr | 184–85 |
| 15 | C(Cl)=CH | H | $CF_3$ | Et | 813–84 |
| 16 | $CH_2CH_2$ | H | $CF_3$ | Me | 101–04 |
| 17 | $CH_2CH_2$ | H | $CH_3$ | Et | 122–27 |
| 18 | $OC(CH_3)_2$ | H | $OCF_3$ | H | 155 |

TEST A

Fall Armyworm

Test units, each consisting of a H.I.S. (high impact sytrene) trays with 16 cells were prepared. In 12 of the cells is placed wet filter paper and approximately 8 cm² of lima leaf, in the other 4 cells is a 0.5 cm layer of wheat germ diet. Fifteen to twenty third instar larvae of fall armyworm (*Spodoptera frugiperda*) were placed in a 8 ounce (230 mL) plastic cup. Solutions of each of the test compounds in 75/25 acetone/distilled water solvent were sprayed into the tray and cup. Spraying was accomplished by passing the tray and cup, on a conveyor belt, directly beneath a flat fan hydraulic nozzle which discharged the spray at a rate of 0.5 pounds of active ingredient per acre (about 0.55 kg/ha) at 30 psi (207 kPa). The insects were transferred into the tray (one insect per cell). The trays were covered and held at 27° C. and 50% relative humidity for 48 hours after which time readings were taken on the 12 cells with lima leaves. The 4 remaining cells were read at 7 days for a delayed toxicity reading. Of the compounds tested, the following gave mortality levels of 80% or higher: 6, 7, 8, 9, 10, 12, 17, 19.

TEST B

Tobacco Budworm

The test procedure for Test A was repeated for efficacy against third instar tobacco budworm (*Heliothis virescens*) except that three 8 ounce (230 mL) plastic cups with wheat germ diet were used in place of the HIS tray, with each cup preinfested with 5 third instar larvae. Of the compounds tested, the following gave mortality levels of 80% or higher: 19.

TEST C

Southern Corn Rootworm

Units consisting of an 8-ounce (230 mL) plastic cup containing 1 one-inch square of a soybean-wheatgerm diet were prepared. The test units were sprayed as described in Test A with individual solutions of the test compounds. After the spray on the cups had dried, five second-instar larvae of the southern corn rootworm (*Diabrotica undecimpunctata howardi*) were placed into each cup. The cups were then covered and held at 27° C. and 50% relative humidity for 48 hours, after which time mortality readings were taken. Of the compounds tested, the following gave mortality levels of 80% or higher: 1, 2, 6, 7, 8, 9, 10, 11, 12, 13, 14, 15, 16, 17.

TEST D

Boll Weevil

Five adult boll weevils (*Anthonomus grandis grandis*) were placed into each of a series of 9-ounce (260 mL) cups. The test units were sprayed as described in Test A with individual solutions of the below-listed compounds. Each cup was then covered with a vented lid and held at 27° C. and 50% relative humidity for 48 hours, after which time mortality readings were taken. Of the compounds tested, the following gave mortality levels of 80% or higher: 2, 6, 7, 8, 9, 10, 11, 15, 16, 17.

TEST E

Aster Leafhopper

Test units were prepared from a series of 12-ounce (350 mL) cups, each containing oat (*Avena sativa*) seedlings in a 1-inch (2.5 cm) layer of sterilized soil and a ½ inch layer of sand. The test units were sprayed as described in Test A with individual solutions of the compounds. After the oats had dried from the spraying, between 10 and 15 adult aster leafhoppers (*Mascrosteles fascifrons*) were aspirated into each of the cups covered and vented lids. The cups were held at 27° C. and 50% relative humidity for 48 hours, after which time mortality readings were taken. Of the compounds tested, the following gave mortality levels of 80% or higher: 17.

We claim:

1. A compound of the formula

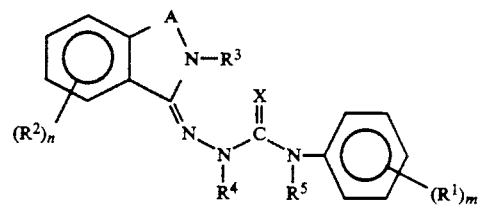

wherein:

A is selected from the group O, $SO_2$, C(O), $CH_2$, $CH_2CH_2$, CH=CH, and $OCH_2$, wherein each hydrogen attached to a ring carbon can be optionally replaced with a substituent independently selected from the group halogen, $C_1-C_6$ alkyl, $C_3-C_6$ cycloalkyl, $C_1-C_6$ haloalkyl, $C_3-C_6$ halocycloalkyl, $C_4-C_7$ cycloalkylalkyl, $C_2-C_4$ alkoxycarbonyl and phenyl, wherein phenyl can be optionally substituted with 1 to 3 substituents independently selected from W;

X is selected from the group O and S;

$R^1$ and $R^2$ are independently selected from the group H, $C_1-C_6$ alkyl, $C_1-C_6$ haloalkyl, $C_3-C_6$ cycloalkyl, $C_3-C_6$ halocycloalkyl, $C_4-C_7$ cycloalkylalkyl, $C_4-C_7$ halocycloalkylalkyl, $C_2-C_6$ alkenyl, $C_2-C_6$ haloalkenyl, $C_2-C_6$ alkynyl, $C_2-C_6$ haloalkynyl, $C_2-C_6$ alkoxyalkyl, $C_1-C_6$ alkylthio, $C_2-C_6$ alkylthioalkyl, $C_1-C_6$ nitroalkyl, $C_2-C_6$ cyanoalkyl, $C_3-C_8$ alkoxycarbonylalkyl, halogen, CN, $NO_2$, $N_3$, SCN, $OR^6$, $SR^6$, $S(O)R^6$, $S(O)_2R^6$, $N(R^7)R^8$, $C(O)R^6$, $C(O)OR^6$, $C(O)N(R^7)R^8$, $OC(O)R^6$, $OC(O)OR^6$, $OC(O)N(R^7)R^8$, $N(R^9)C(O)R^7$, $N(R^9)C(O)N(R^7)R^8$, $OS(O)_2R^7$, $N(R^8)S(O)_2R^7$; and phenyl or benzyl each optionally substituted with 1 to 3 substituents independently selected from W; when m is 2, $R^1$ is optionally taken together as $OCH_2O$, $OCH_2CH_2O$ or $CH_2CH_2O$ to form a 5- or 6-membered fused ring, each carbon optionally substituted with 1 or 2 substituents independently selected from the group halogen and methyl; when n is 2, $R^2$ is optionally taken together as $OCH_2O$, $OCH_2CH_2O$ or $CH_2CH_2O$ to form a 5- or 6-membered fused ring, each carbon optionally substituted with 1 or 2 substituents independently selected from the group halogen and methyl;

$R^3$ is selected from the group H, $C_1-C_6$ alkyl, $C_1-C_6$ haloalkyl, $C_2-C_6$ alkylcarbonyl and $C_2-C_6$ alkoxycarbonyl; $C_1-C_6$ alkyl substituted with a group selected from CN, $NO_2$, $C_1-C_4$ alkoxy, $C_1-C_4$ haloalkoxy, $C_1-C_4$ alkylthio and $C_2-C_4$ alkoxycarbonyl; and phenyl and benzyl each optionally substituted with 1 to 3 substituents independently selected from W;

$R^4$ and $R^5$ are independently selected from the group H, $C_1-C_6$ alkyl, $C_1-C_6$ haloalkyl, $C_3-C_6$ cycloalkyl, $C_3-C_6$ halocycloalkyl, $C_4-C_7$ cycloalkylalkyl, $C_4-C_7$ halocycloalkylalkyl, $C_2-C_6$ alkoxyalkyl, $C_2-C_6$ alkenyl, $C_2-C_6$ alkynyl, CHO, $C_2-C_6$ alkylcarbonyl, $C_2-C_6$ alkoxycarbonyl, $C(O)R^{18}$, $C(O)OR^{18}$, $C_1-C_6$ alkylthio, $C_1-C_6$ haloalkylthio, phenylthio, $R^{11}OC(O)N(R^{12})S$-, $R^{13}(R^{14})NS$-, $N=C(R^{15})R^{16}$, $OR^6$, and $N(R^{15})R^{16}$; $C_1-C_6$ alkyl substituted with a group selected from CN, NO$_2$, C$_1$-C$_4$ haloalkoxy, C$_1$-C$_4$ alkylthio, C$_1$-C$_4$ alkylsulfinyl, C$_1$-C$_4$ alkylsulfonyl, C$_2$-C$_4$ alkylcarbonyl and C$_2$-C$_4$ alkoxycarbonyl; and phenyl and benzyl each optionally substituted with 1 to 3 substituents independently selected from W;

R$^6$ and R$^7$ are selected from the group H, C$_1$-C$_6$ alkyl, C$_1$-C$_6$ haloalkyl, C$_4$-C$_7$ cycloalkylalkyl, C$_4$-C$_7$ halocycloalkylalkyl, C$_2$-C$_6$ alkenyl, C$_2$-C$_6$ halolalkenyl, C$_2$-C$_6$ alkynyl, C$_2$-C$_6$ haloalkynyl, C$_2$-C$_6$ alkoxyalkyl, C$_2$-C$_6$ alkylthioalkyl, C$_1$-C$_6$ nitroalkyl, C$_2$-C$_6$ cyanoalkyl, C$_3$-C$_8$ alkoxycarbonylalkyl, C$_3$-C$_6$ cycloalkyl and C$_3$-C$_6$ halocycloalkyl; and phenyl and benzyl each optionally substituted with 1 to 3 substituents independently selected from W;

R$^8$ and R$^9$ are independently selected from the group H, C$_1$-C$_4$ alkyl, C$_2$-C$_4$ alkenyl, C$_2$-C$_4$ alkynyl; or when R$^7$ and R$^8$ are attached to the same atom they can optionally be taken together as —CH$_2$CH$_2$CH$_2$CH$_2$—, —CH$_2$CH$_2$CH$_2$CH$_2$CH$_2$— or —C$_2$CH$_2$OCH$_2$CH$_2$—;

R$^{11}$ is C$_1$-C$_6$ alkyl;

R$_{12}$ is C$_1$-C$_4$ alkyl;

R$^{13}$ and R$^{14}$ are independently C$_1$-C$_4$ alkyl; or R$^{13}$ and R$^{14}$ can be taken together as —CH$_2$CH$_2$CH$_2$CH$_2$CH$_2$— or —CH$_2$CH$_2$OCH$_2$CH$_2$—;

R$^{15}$ is selected from the group H, C$_1$-C$_4$ alkyl and C(O)R$^{17}$;

R$^{16}$ is selected from the group H, C$_1$-C$_4$ alkyl, C$_1$-C$_4$ haloalkyl; and phenyl optionally substituted with 1 to 3 substituents independently selected from W; or R$^{15}$ and R$^{16}$ can be taken together as —CH$_2$CH$_2$CH$_2$—, —CH$_2$CH$_2$CH$_2$CH$_2$— or —CH$_2$CH$_2$CH$_2$CH$_2$—;

R$^{17}$ is selected from the group H, C$_1$-C$_6$ alkyl, C$_1$-C$_6$ alkoxy, C$_1$-C$_6$ haloalkyl, C$_2$-C$_6$ alkenyl, C$_2$-C$_6$ haloalkenyl, C$_2$-C$_6$ alkynyl, C$_3$-C$_6$ haloalkynyl, C$_2$-C$_6$ alkoxyalkyl, C$_2$-C$_6$ alkylthioalkyl, C$_1$-C$_6$ nitroalkyl, C$_2$-C$_6$ cyanoalkyl; C$_3$-C$_8$ alkoxycarbonylalkyl, C$_3$-C$_6$ cycloalkyl, C$_3$-C$_6$ halocycloalkyl; and phenyl and benzyl each optionally substituted with 1 to 3 substituents independently selected from W;

R$^{18}$ is phenyl optional substituted with 1 to 3 substituents independently selected from W;

W is selected from the group halogen, CN, N(R$^7$)R$^8$, NO$_2$, C$_1$-C$_2$ alkyl, C$_1$-C$_2$ haloalkyl, C$_1$-C$_2$ alkoxy, C$_1$-C$_2$ haloalkoxy, C$_1$-C$_2$ alkylthio, C$_1$-C$_2$ haloalkylthio, C$_1$-C$_2$ alkylsulfonyl and C$_1$-C$_2$ haloalkylsulfonyl;

m is 1 to 3; and n is 1 or 2.

2. A compound according to claim 1 wherein:

R$^1$ and R$^2$ are independently selected from the group halogen, C$_1$-C$_6$ haloalkyl and C$_1$-C$_6$ haloalkoxy;

R$^3$ is selected from the group C$_1$-C$_6$ alkyl; and phenyl optionally substituted with a substituent selected from halogen, C$_1$-C$_2$ haloalkyl and C$_1$-C$_2$ haloalkoxy;

R$^4$ and R$^5$ are H; and

X is O.

3. An arthropodicidal composition comprising an arthropodicidally effective amount of a compound according to claim 1 and a carrier therefor.

4. An arthropodicidal composition comprising an arthropodicidally effective amount of a compound according to claim 2 and a carrier therefor.

5. A method for controlling arthropods comprising contacting the arthropods or their environment with an arthropodicidally effective amount of a compound according to claim 1.

6. A method for controlling arthropods comprising contacting the arthropods or their environment with an arthropodicidally effective amount of a compound according to claim 2.

* * * * *